_United States Patent_ [19]

Waller

[11] 4,446,329

[45] May 1, 1984

[54] ALKYLATION OR AROMATIC COMPOUNDS

[75] Inventor: Francis J. Waller, Wilmington, Del.

[73] Assignee: E. I. Du Pont de Nemours & Company, Wilmington, Del.

[21] Appl. No.: 478,543

[22] Filed: Mar. 24, 1983

[51] Int. Cl.$^3$ .............................................. C07C 2/66
[52] U.S. Cl. .................................................. 585/458
[58] Field of Search ........................................ 585/458

[56] References Cited

U.S. PATENT DOCUMENTS

| | | | |
|---|---|---|---|
| 3,116,346 | 12/1963 | Van Dyke | 585/458 |
| 3,479,322 | 11/1969 | Petersen | 585/458 |
| 4,022,847 | 5/1977 | McClure | 585/458 |
| 4,038,213 | 7/1977 | McClure et al. | 252/430 |
| 4,041,090 | 8/1977 | McClure | 585/458 |
| 4,060,565 | 11/1977 | McClure et al. | 260/671 C |
| 4,287,376 | 9/1981 | Shimizu et al. | 585/458 |
| 4,316,997 | 2/1982 | Vaughan | 585/458 |
| 4,356,318 | 10/1982 | Waller | 562/406 |

FOREIGN PATENT DOCUMENTS 2090856  7/1982  United Kingdom ............... 585/458

OTHER PUBLICATIONS

Research Disclosure, Jul. (1980), pp. 270–271.
Olah et al., J. Org. Chem. 42, pp. 4187–4191, (1977).
Olah et al., Synthesis, pp. 671–672, (Sep. 1978).
Krespan, J. Org. Chem. 44, pp. 4924–4929, (1979).
Grot, Research Disclosure, (Aug.), 1982, p. 280.
Kamm, Research Disclosure, (Aug.), 1982, pp. 280–281.
Peluso, Research Disclosure, (Sep.), 1982, p. 311.
Peluso, Dissertation Abstracts International 41, pp. 4536B–4537B, (Jun. 1981).
Kelly et al., Du Pont Innovation 4, (No. 2), pp. 4–7, (1973).
Du Pont Nafion® Perfluorosulfonic Acid Bulletin, Feb. 1976, Table 1.
Olah in Part II of "Friedel–Crafts and Related Reactions," Interscience Publishers (1964).
Olah et al., J. Org. Chem. 47, pp. 596–598, (1982).

_Primary Examiner_—Delbert E. Gantz
_Assistant Examiner_—Cynthia A. Prezlock

[57] ABSTRACT

Improved catalytic process for the alkylation of aromatic substrates, the improved process characterized in that the catalyst is a metal cation salt of a perfluorosulfonic acid polymer having an equivalent weight of about 500 to about 20,000, the metal cation having a log $K_{11}$ greater than $-10$.

15 Claims, No Drawings

4,446,329

ALKYLATION OR AROMATIC COMPOUNDS

BACKGROUND OF THE INVENTION

1. Field of the Invention

This invention relates to an improved process for the alkylation of aromatic substrates. In particular, it relates to a process using selected metal cation salts of perfluorosulfonic acid polymers as alkylation catalysts.

2. Background

The catalytic alkylation of aromatic substrates is well known in the art and cannot be discussed in detail in this specification. The following limited number of publications provides adequate background for an understanding of the invention herein.

Research Disclosure, July (1980), p. 270-271, summarizes the known catalytic uses, including the alkylation of aromatic hydrocarbons, of polymers containing perfluorosulfonic acid groups.

Olah et al., J. Org. Chem. 42, p. 4187-4191 (1977), disclose the use of perfluorosulfonic acid polymers as ethylation catalysts for benzene; the thermal stability of the catalyst rapidly decreases at about 220° C.

Olah et al., J. Org. Chem. 47, p. 596-598 (1982), disclose the use of a mercury (II)-impregnated perfluorosulfonic acid polymer in nitration of aromatics with nitric acid, and Olah et al., Synthesis, p. 671-672 (September, 1978), disclose the use of a mercury (II)-impregnated perfluorosulfonic acid polymer as an alkyne hydration catalyst.

U.S. Pat. Nos. 4,022,847 and 4,041,090 disclose that, in the alkylation of benzene to ethylbenzene using a perfluorosulfonic acid polymer as catalyst, the reaction temperature must be kept below about 225° C. due to the lack of stability of the catalyst at temperatures above 250° C.

U.S. Pat. Nos. 4,038,213 and 4,060,565 disclose the use of a supported perfluorosulfonic acid polymer as a catalyst for the alkylation of benzene. The temperature must be kept below about 205° C. to avoid serious catalyst deactivation, as judged by decreased olefin conversion.

Krespan, J. Org. Chem. 44, p. 4924-4929 (1979), discloses the alkylation of selected aromatic substrates using a perfluorosulfonic acid polymer catalyst.

U.S. Pat. No. 4,356,318 discloses the use of Group VIII metal cations of perfluorosulfonic acid polymers as catalysts for the oxidative carbonylation of toluene to toluic acid.

Grot, Research Disclosure, (August) 1982, p. 280, discloses the preparation of cation salts of perfluorosulfonic acid polymers with such metals as nickel, palladium, and platinum. The metal salts are reduced to the metal, and the product may be used as a catalyst.

Kamm, Research Disclosure, (August) 1982, p. 280-281, discloses the conversion of sulfonic acid groups of a polymeric perfluorosulfonic acid to the sulfonate salt of a catalytically active metal.

Peluso, Research Disclosure, (September) 1982, p. 311, discloses porous supported catalysts prepared from perfluorosulfonic acid polymers and metal ions such as transition metal ions, for example, palladium.

Peluso, Dissertation Abstracts International 41, p. 4536B-4537B (June 1981), discloses the reaction of $Cu^{+2}$ and Pd(II) perfluorosulfonic acid ionomers with carbon monoxide and nitric oxide, and the Pd(II) ionomer with ethylene.

Kelly et al., Du Pont Innovation 4, (No. 2), p. 4-7 (1973), disclose the use of Nafion ® perfluorosulfonic acid copolymer membranes as cation exchange membranes in Donnan dialysis.

Du Pont Nafion ® perfluorosulfonic acid product bulletin, February 1976, Table 1, discloses water absorbtion of the cation form of the Nafion ® membrane with a number of cations.

Alkylation of aromatic substrates in the presence of a Lewis acid catalyst is well-known, and this general reaction is reviewed by Olah in Part II of "Friedel-Crafts and Related Reactions," Interscience Publishers (1964). More recently, as is evident from the aforesaid publications, it has been discovered that a perfluorosulfonic acid polymer can be employed as the Lewis acid catalyst. The use of such a catalyst avoids the corrosiveness of the commercially important catalyst systems based on aluminum chloride and aluminum chloride/-hydrochloric acid. However, the catalyst systems based on a perfluorosulfonic acid polymer appear to have a maximum useful operating temperature of about 225° C. Above that temperature the catalyst lacks thermal stability, and the yields and conversions of the products and starting materials, respectively, are decreased.

It is an object of this invention to provide an improved process for the alkylation of aromatic substrates. Another object is to provide such a process which avoids the corrosive environment which is normally associated with aluminum chloride-based catalyst systems. Still another object is to provide such a process which employs a type of perfluorosulfonic acid polymer catalyst system which is operable at much higher temperatures than the perfluorosulfonic acid polymer systems currently known in the art. These and other objects will be apparent from the following description of the invention.

DETAILED DESCRIPTION OF THE INVENTION

The present invention resides in an improved process for the alkylation of an aromatic compound with an alkylating agent in the presence of a Lewis acid catalyst, the improvement comprising employing as the catalyst a metal cation salt of a perfluorosulfonic acid polymer.

In the process of the instant invention, it has been found that the use of a certain metal cation salt of a perfluorosulfonic acid polymer allows alkylation to be carried out at significantly higher temperatures, e.g., temperatures as high as about 350° C. The catalyst will be described in detail hereinafter. Even at such elevated temperatures, many of the catalysts of the invention are recoverable as a powder suitable for use in subsequent alkylation reactions. The use of higher reaction temperatures allows the alkylation reaction to proceed at an increased rate with more efficient use of the reaction vessel.

In addition to the advantage of being able to carry out the alkylation at higher temperatures, use of selected metal cation salts as catalysts herein gives a significant increase in reaction rate, compared with a conventional perfluorosulfonic acid polymer catalyst at the same temperature. Increased reaction rate is measured by catalyst turnover rate, expressed as mols of product obtained/mol of metal cation/hour.

The alkylation reaction is applicable to a wide variety of aromatic substrates, including both substituted and unsubstituted mononuclear and polynuclear compounds suitable as substrates in Friedel-Crafts alkylation reactions. Such substrates include, but are not limited to, benzene, toluene, o-, m-, and p-xylene, ethylbenzene, cumene, p-cymene, diethylbenzene, triethylbenzene, mesitylene, t-butylbenzene, p-ethyltoluene, pseudocumene, cyclohexylbenzene, indane, bromobenzene, chlorobenzene, iodobenzene, fluorobenzene, p-chlorotoluene, phenol, p-cresol, m-cresol, 2,5-dimethylphenol, anisole, diphenyl ether, 4-chloroanisole, 4-methoxyphenol, aniline, p-toluidine, naphthalene, 1-methylnaphthalene, tetrahydronaphthalene, biphenyl, dibenzyl, anthracene, 1-methylanthracene, and phenanthrene. Preferred aromatic substrates include both substituted and unsubstituted benzenes, with benzene being particularly preferred.

Alkylation according to the process of the invention can be carried out with any of the usual alkylating agents employed in Friedel-Crafts alkylation reactions, including, but not limited to, alkenes, alkadienes, and alkynes. Preferred alkylating agents include alkenes of 2-6 carbon atoms, such as ethylene, propene, 1-butene, 2-butene, 2-methyl-1-propene, 1-pentene, 2-pentene, and 1-hexene. Ethylene is particularly preferred.

The molar ratio of aromatic substrate to alkylating agent employed in the process of the invention is not critical, and it can be varied over wide limits. When mono-alkylated products are desired, it is preferred to employ an excess of aromatic substrate, for example, about 1 to about 20 mols of substrate per mol of alkylating agent, and even more preferably, about 3 to about 12 mols of substrate per mol of alkylating agent. Conversely, an excess of alkylating agent over aromatic substrate favors the formation of polyalkylated products.

The catalyst employed in the improved process of the invention requires a metal cation salt of a perfluorosulfonic acid polymer. Suitable metal cations are selected from those which have log $K_{11}$ greater than -10 as shown in FIG. 18.4 p. 408, of the book by Baes et al., "The Hydrolysis of Cations," John Wiley & Sons, New York (1976). The hydrolysis constant, $K_{11}$, as shown on p. 403 of Baes et al., is calculated from the equation, shown on pages 401 and 403,

$$M(OH_2)_n{}^{z+} \rightleftharpoons MOH(OH_2)_{n-1}{}^{(z-1)30} + H^+$$

wherein M is the selected metal cation and z is the valence of M.

Preferred metal cations include $Al^{3+}$, $Zn^{2+}$, $Fe^{3+}$, $Cu^{2+}$, $Sn^{2+}$, $Cr^{3+}$, $Co^{2+}$, and $Hg^{2+}$, with $Cr^{3+}$, $Sn^{2+}$, $Al^{3+}$, and $Fe^{3+}$ being particularly preferred because of the superior reaction rates obtained with them.

Preferred perfluorosulfonic acid polymers which can be employed as the anion component of the catalyst have a number average molecular weight of at least about 5000. The polymer must contain a sufficient number of sulfonic acid groups to give an equivalent weight of about 500 to about 20,000, preferably about 900 to about 2000. Although the polymer backbone comprises, for the most part, fluorinated carbon atoms, it is not necessary that all other atoms be excluded. For example, ether oxygen atoms may be present in the backbone, as well as in the side chains of the polymer. Such other atoms and/or groups as hydrogen (H), chlorine (Cl) and carboxyl (COOH) may be present in limited amounts without significantly affecting the stability or operability of the polymer under the process conditions. It is preferred that the polymer contain no greater than about 5 weight percent total of hydrogen, chlorine and carboxyl groups. Perfluorosulfonic acid polymers may be employed in powder or film form.

In general, the metal cation salt of the perfluorosulfonic acid polymer is employed in a ratio of about 25 to about 500 mols of alkylating agent per mol of catalyst, preferably about 50 to about 200 mols.

Although a solvent is not required for the alkylation reaction, it may be advantageous, particularly when a higher molecular weight liquid or solid aromatic compound is employed as the substrate. Alternatively, particularly when lower molecular weight aromatic substrates are employed, an excess quantity of aromatic compound may serve as the solvent. If a solvent is employed, an important factor to be considered is the boiling point difference between the solvent and the alkylated products. The boiling point difference should be such as to enable efficient separation of the solvent and reaction products by simple distillation. Suitable solvents include, but are not limited to, carbon disulfide and aliphatic fluorocarbons.

The alkylation reaction of this invention can be effected by heating the aromatic compound, alkylating agent, catalyst, and solvent, if present, at a temperature of about 140° to about 350° C., preferably about 200° to about 300° C.

The alkylation reaction conveniently can be carried out for as long as about 2 hours, but 6 to 30 minute reaction periods generally suffice and are preferred.

The process of this invention can be carried out readily in liquid or gas phase using well-known chemical engineering practice, which includes continuous, semi-continuous, and batch operations. Reaction vessels used in the process are not critical as long as they are able to withstand the temperatures and pressures employed. Pressure vessels of high tensile steel are generally used and they may be either lined or unlined. Suitable reactor liners include, but are not limited to, Hastelloy ® metals, stainless steel, silver, copper, tantalum, glass and glazed ceramics.

The following are illustrative examples of the invention in which all parts and percentages are by weight and all degrees are Celsius unless otherwise noted. The yield of product is defined as mols product/mols olefin charged $\times 10^2$.

Metal ion salts of perfluorosulfonic acid polymers were prepared by Procedure A.

PROCEDURE A

Perfluorosulfonic Acid Polymer Preparation

A slurry of 100 g of the potassium salt of a perfluorosulfonic acid polymer (Du Pont Nafion ®511 perfluorosulfonic acid powder), 130 mL of concentrated hydrochloric acid, and 400 mL of distilled water was heated at 60° for 2 h with stirring. The solution was decanted, and the residual solid polymer was treated two additional times with aqueous hydrochloric acid, as described above. The residual polymer slurry was cooled and the polymer was separated by filtration and washed with distilled water (~1,000 mL) until the filtrate was neutral. The product was dried at 110° in a vacuum oven for about 6 h under nitrogen. The dried perfluorinated ion exchange polymer (PFIEP) weighed 92 g and had an equivalent weight of 1,099 by titration.

Metal Salt Preparation

A solution of the designated metal salt in 200 mL of distilled water was stirred with PFIEP powder for about 3 h at 60°-70°. The polymer was separated and retreated with another portion of exchanging metal salt solution for an additional 3 h. The polymer salt was separated by filtration, washed with about 25 mL of distilled water, and dried at about 100° in a vacuum oven for about 6 h under nitrogen. The product was analyzed for cation content using conventional analytical procedures. The metal salts prepared are summarized in Table 1.

TABLE 1
METAL SALTS OF PFIEP

| Salt Designation | Exchanging Metal Salt (mmol) | PFIEP (mequiv) | Metal Salt of PFIEP (g) | Percent Cation |
|---|---|---|---|---|
| A | Al(NO$_3$)$_3$.9H$_2$O 3.3 | 10.4 | 10.64 | 0.69 (Al) |
| B | Zn(NO$_3$)$_2$.6H$_2$O 10.0 | 20.7 | 22.6 | 3.02 (Zn) |
| C | Al(NO$_3$)$_3$.9H$_2$O 6.7 | 20.7 | 20.7 | 0.77 (Al) |
| D | Al(NO$_3$)$_3$.9H$_2$O 6.7 | 20.7 | 22.0 | 0.67 (Al) |
| E | Fe(NO$_3$)$_3$.9H$_2$O 6.7 | 20.7 | 22.0 | 1.89 (Fe) |
| F | Cu(NO$_3$)$_2$.3H$_2$O 5.2 | 10.0 | 10.8 | 2.95 (Cu) |
| G | SnCl$_2$ 10.0 | 19.1 | 23.6 | 4.58 (Sn) |
| H | Cr(NO$_3$)$_3$.9H$_2$O[1] 3.33 | 10.0 | 10.7 | 1.38 (Cr) |
| I | Co(NO$_3$)$_2$.6H$_2$O 10.0 | 20.0 | 20.7 | 2.38 (Co) |
| J | Zn(NO$_3$)$_2$.6H$_2$O 10.0 | 20.0 | 20.5 | 2.94 (Zn) |
| K | SnCl$_2$[1] 10.0 | 20.0 | 21.3 | 3.55 (Sn) |
| L | HgO[1] 10.1 | 20.0 | 23.2 | 8.06 (Hg) |
| M | Fe(NO$_3$)$_3$.9H$_2$O 6.7 | 20.7 | 22.0 | 1.68 (Fe) |
| N[2] | Fe(NO$_3$)$_3$.9H$_2$O 6.7 | 20.0 | 20.8 | 1.87 (Fe) |
| O | Zn(NO$_3$)$_2$.6H$_2$O 10.0 | 20.0 | 22.4 | 3.15 (Zn) |

[1]Only one metal salt solution exchange was used.
[2]The metal salt prepared was heated to 250° to remove water of hydration before being used as a catalyst. An 11 percent weight loss was observed on heating.

General Procedure for Alkylation of Aromatic Substrates

A 330 mL Hastelloy® C-lined shaker tube was flushed with nitrogen and 5 g of the designated metal salt of PFIEP catalyst and 677 mmol of aromatic substrate were charged. The tube was cooled to −78°, evacuated, and a designated olefin was condensed into the tube. The tube was sealed and heated at autogeneous pressure under the chosen reaction conditions. After reaction completion the tube was cooled to room temperature, and the catalyst was removed by filtration. The liquid product was analyzed by a standard gas chromatographic procedure using a 30.5×0.32 cm column of 10% SE-30 on 80/100 mesh diatomaceous earth support. A temperature program of 110° to 220° was utilized with a helium flow of about 30 mL/min. Response factors referenced against toluene (internal standard) were employed to calculate the yield of product.

EXAMPLE 1

A mixture of the aluminum salt A and benzene was heated with 500 mmol of ethylene at 140° for 1 h by the general procedure for alkylation described above. A 2.0 percent yield of ethylbenzene was obtained. Analysis for higher alkylated products was not carried out.

EXAMPLES 2–16

These Examples illustrate a variety of metal salt catalysts, selected from Table 1, that may be employed in the alkylation reaction. The aforesaid general alkylation procedure was employed with 677 mmol of benzene and 143 mmol of ethylene. In most of the Examples, the metal salt of PFIEP was recovered as a powder. Higher alkylated products represent, in most cases, a mixture of diethylbenzene, triethylbenzene, tetraethylbenzene, and sec-butylbenzene. The results are summarized in Table 2.

TABLE 2
ETHYLATION OF BENZENE

| Ex. | Metal Salt of PFIEP | Reaction Conditions Temp. (°C.) | Time (h) | Product Yield, Percent Ethylbenzene | Higher Alkylated Products |
|---|---|---|---|---|---|
| 2 | C | 180 | 0.5 | 33.7 | 1.7 |
| 3 | D | 240 | 0.25 | 39.8 | 6.8 |
| 4 | D | 280 | 0.5 | 49.5 | 6.3 |
| 5 | B | 240 | 0.25 | 57.3 | 11.2 |
| 6 | G | 240 | 0.5 | 49.2 | —[1] |
| 7 | E | 240 | 0.25 | 48.3 | 13.8 |
| 8 | M | 240 | 0.5 | 55.5 | 10.3 |
| 9 | H | 240 | 0.25 | 65.7 | 7.7 |
| 10[2] | F | 240 | 0.5 | 48.9 | 14.7 |
| 11 | I | 240 | 0.25 | 53.9 | 11.8 |
| 12 | N | 300 | 0.25 | 56.4 | 6.9 |
| 13 | J | 300 | 0.25 | 62.7 | 13.3 |
| 14 | K | 240 | 0.25 | 61.3 | 11.3 |
| 15 | J | 190 | 0.25 | No Reaction was observed | |
| 16[2] | L | 240 | 0.25 | 57.6 | 9.5 |
| Control A[3] | —[4] | 180 | 0.5 | 56.5 | 1.1 |
| Control B[2] | —[4] | 240 | 0.25 | 56.9 | 5.6 |

[1]The higher alkylated products were not determined.
[2]The recovered metal salt (or resin) was fused together.
[3]The recovered resin showed some fusion.
[4]The metal salt was replaced with 5 g of PFIEP resin.

EXAMPLE 17

The aforesaid general alkylation procedure was employed with 677 mmol of benzene, 143 mmol of propene, and 5 g of iron metal salt N. The reaction was carried out at 240° for 0.25 h. A 50.9% yield of i-propylbenzene and an 8.0% yield of diisopropylbenzene were obtained, and the iron salt catalyst was recovered in powder form.

EXAMPLE 18

The general alkylation procedure was employed with 677 mmol of toluene, 143 mmol of ethylene and 5 g of zinc metal salt O. The reaction was carried out at 240° for 0.25 h. The products obtained were p-ethyltoluene (32.9%), other mixed ethyltoluenes (23.9%), and a mixture of di-, tri-, and tetra-ethyltoluenes (11%).

Turnover Rate Comparison For Alkylation Catalyst

Catalyst turnover rates, i.e., mols product/mol metal cation/h, for several of the Examples summarized in Table 2 were calculated. The term "mols product" in the turnover rate expression is defined as Σ(mols φEt+2[mols φ(Et)$_2$]+3[mols φ(Et)$_3$]+4[mols φ(Et)$_4$]+mols φC$_4$H$_9$). The di-, tri-, and tetraethylbenzenes represent the total mol amount for all the isomers. The abbreviation "φC$_4$H$_9$" is used for sec-butylbenzene. The results are summarized in Table 3.

TABLE 3

| | CATALYST TURNOVER RATES | |
|---|---|---|
| Ex. | Catalyst Cation | Turnover Rate |
| 9 | $Cr^{3+}$ | 374 |
| 14 | $Sn^{2+}$ | 328 |
| 3 | $Al^{3+}$ | 248 |
| 7 | $Fe^{3+}$ | 233 |
| 11 | $Co^{2+}$ | 229 |
| 5 | $Zn^{2+}$ | 201 |
| 16 | $Hg^{2+}$ | 222 |
| 10 | $Cu^{2+}$ | 98 |
| Control B | $H^+$ | 87 |

BEST MODE FOR CARRYING OUT THE INVENTION

The best mode presently contemplated for carrying out the invention is represented by Examples 3, 7, 9, and 14.

INDUSTRIAL APPLICABILITY

Alkylated aromatic products are employed as intermediates in a variety of industrial applications. For example, ethylbenzene is the precursor of styrene, widely used in polymeric form in synthetic rubber and resins. p-Xylene is a precursor for terephthalic acid; toluene is used in the manufacture of dyes; and cumene is used for the preparation of acetone and phenol.

I claim:

1. Improved catalytic process for the alkylation of aromatic substrates, the improved process characterized in that it is carried out at at least 200° C. and the catalyst is a metal cation salt of a perfluorosulfonic acid polymer having an equivalent weight of about 500 to about 20,000, the metal cation having a log $K_{11}$ greater than -10.

2. Process of claim 1 wherein the alkylating agent is selected from alkenes, alkadienes and alkynes and the substrate is selected from mono-, di-, and tricyclic aromatic compounds.

3. Process of claim 1 wherein the ratio of alkylating agent to metal cation salt of perfluorosulfonic acid polymer is, on a molar basis, about 25:1 to about 500:1.

4. Process of claim 3 wherein the ratio is about 50:1 to about 200:1.

5. Process of claim 1 carried out in the presence of a solvent.

6. Process of claim 5 wherein the solvent is the aromatic substrate.

7. Process of claim 1 which is carried out at about 200° C. to about 300° C.

8. Process of claim 1 wherein the alkylating agent is an alkene of 2-6 carbon atoms and the aromatic substrate is benzene or a substituted benzene.

9. Process of claim 1 wherein the ratio of substrate to alkylating agent is, on a molar basis, about 1:1 to about 20:1.

10. Process of claim 1 wherein the ratio of substrate to alkylating agent is, on a molar basis, about 3:1 to about 12:1.

11. Process of claim 1 wherein the alkylating agent is ethylene and the aromatic substrate is benzene.

12. Process of claim 11 wherein the ratio of substrate to alkylating agent is, on a molar basis, about 3:1 to about 12:1 and the metal cation is selected from $Cr^{3+}$, $Sn^{2+}$, $Al^{3+}$, and $Fe^{3+}$.

13. Process of claim 1 wherein the ratio of substrate to alkylating agent is, on a molar basis, less than 1:1.

14. Process of claim 1 wherein the metal cation is selected from $Cr^{3+}$, $Sn^{2+}$, $Al^{3+}$, and $Fe^{3+}$.

15. Process of claim 1 wherein the perfluorosulfonic acid polymer contains no more than 5 weight percent of H, Cl or COOH substituents.